United States Patent

Sardelis et al.

[11] Patent Number: 5,730,732
[45] Date of Patent: Mar. 24, 1998

[54] NON-MAGNETIC STAINLESS STEEL SURGICAL NEEDLE

[75] Inventors: Timothy Sardelis, Somerset; William McJames, Belle Mead, both of N.J.

[73] Assignee: Ethicon, Inc., Somerville, N.J.

[21] Appl. No.: 759,491

[22] Filed: Dec. 4, 1996

[51] Int. Cl.⁶ .................................................. A61M 5/32
[52] U.S. Cl. ........................ 604/272; 606/222; 606/223
[58] Field of Search .................... 604/272, 273, 604/274, 239; 606/222, 223

[56] References Cited

U.S. PATENT DOCUMENTS

| | | |
|---|---|---|
| 5,009,723 | 4/1991 | Honkura et al. |
| 5,139,514 | 8/1992 | Korthoff et al. |
| 5,219,358 | 6/1993 | Bendel et al. |
| 5,330,441 | 7/1994 | Prasad et al. |
| 5,411,613 | 5/1995 | Rizk et al. |
| 5,415,707 | 5/1995 | Bendel et al. |
| 5,458,614 | 10/1995 | Humphrey ............... 604/272 X |
| 5,477,604 | 12/1995 | Smith et al. |
| 5,578,149 | 11/1996 | De Scheerder et al. |
| 5,637,399 | 6/1997 | Yoshikawa et al. ......... 604/272 X |

FOREIGN PATENT DOCUMENTS

| | | |
|---|---|---|
| 2-86788 | 3/1990 | Japan. |
| 3-202628 | 4/1991 | Japan. |
| 3-284264 | 12/1991 | Japan. |
| 4-338470 | 11/1992 | Japan. |

*Primary Examiner*—John D. Yasko
*Attorney, Agent, or Firm*—Emil Richard Skula

[57] ABSTRACT

A non-magnetic surgical needle. The needle is made from Type 316 stainless steel or ERSTE 4456CA stainless steel and is work hardened to have mechanical properties substantially equivalent to a surgical needle made from conventional magnetic stainless steel. The needle is useful in the magnetic field of a magnetic resonance imaging diagnostic apparatus.

4 Claims, 2 Drawing Sheets

NON-MAGNETIC STAINLESS STEEL SURGICAL NEEDLE

TECHNICAL FIELD

The field of art to which this invention relates is surgical needles, in particular, non-magnetic stainless steel surgical needles.

BACKGROUND OF THE INVENTION

The recent use of Magnetic Resonance Imaging (MRI) diagnostic equipment has provided the medical professional with an important, non-invasive diagnostic tool. Magnetic Resonance Imaging operates by placing a patient in a strong magnetic field. The magnetic field excites the protons in tissue to their resonant frequency. Gradient fields tune the frequencies for special differentiation. Radio frequency signals are then transmitted through the tissue to detect resonance differences that distinguish tissue types to make up an image.

Heretofore, it has been difficult to view real time diagnostic images during surgery. X-ray, ultrasound and other forms of imaging all have significant limitations. for most surgical procedures, surgeons had access only to images taken at some time prior to the surgery, hence limiting their usefulness. Advances in the design of MRI equipment have made it possible for a surgeon to stand inside the Magnetic Resonance (MR) magnet and perform surgery while viewing a real time image of the anatomy of interest. Accurate location of internal anatomical structures is important in many surgical procedures, including neurological and gynecological lesion biopsy, orthopaedic endoscopy, laparoscopy, and catheterizations.

Typical surgical procedures already being performed while the patient is in an MRI unit to provide precise visualization include craniotomies in neurosurgery, laminectomies in orthopaedics, and endoscopic sinus procedures in plastic surgery. Other procedures under development include laparoscopies and thoracoscopies. In most of these procedures there is a need to perform suturing as part of the surgical procedure. However, special non-magnetic medical devices and surgical needles must be used because of the extreme strength of the magnetic field in the MRI unit, which can dislodge or otherwise disturb the position of magnetic objects. Conventional stainless steel surgical needles cannot be used in an MRI procedure since they are magnetic. There is a need in this art for non-magnetic surgical needles which can be used in the magnetic field of an MRI.

Non-magnetic surgical needles are known in this art, but are know to have disadvantages. For example, Japanese Patent JP 03284264 A2 911213 discloses a non-magnetic ceramic surgical needle for use in a magnetic resonance imaging magnetic field. However, it is known that such needles are brittle and do not have the mechanical characteristics of conventional stainless steel surgical needles. Non-magnetic needles made from Nickel-Titanium alloys are disclosed in U.S. Pat. No. 5,219,358. Such needles are expensive and difficult to manufacture and may not have the desired physical characteristics. In addition, non-magnetic needles made from Tungsten are disclosed in U.S. Pat. No. 5,415,707. Such needles are difficult to manufacture.

There is a need in this art for non-magnetic stainless steel surgical needles having the mechanical characteristics of conventional stainless steel needles which can be used in MRI magnetic fields.

DISCLOSURE OF THE INVENTION

Therefore, it is an object of the present invention to provide a non-magnetic stainless steel surgical needle which can be used in the magnetic field of an MRI diagnostic unit.

It is yet a further object of the present invention to provide a surgical needle which is non-magnetic and which is made from Type 316 stainless steel alloy or ERSTE Type 4456 CA stainless steel alloy.

It is still yet a further object of the present invention to provide a surgical needle made from Type 316 stainless steel alloy or ERSTE Type 4456 CA stainless steel alloy having the mechanical characteristics of a surgical needle made from conventional stainless steel alloys.

Accordingly, a nonmagnetic surgical needle is disclosed. The surgical needle has an elongated body, a distal piercing point, and a proximal suture mounting end. The surgical needle is made from Type 316 stainless steel alloy which is sufficiently work-hardened such that it has an ultimate tensile strength of at least 250,000 pounds per square inch, and a bending strength in the range of about $7.5 \times 10^{-5}$ inch-pounds to about 8.8 inch-pound over the range of common needle sizes. The needle has a modulus of elasticity (E) of at least $25 \times 10^6$ pounds per square inch and a yield strength of at least 200,000 pounds per square inch. The needle has sufficient ductility to effectively permit it to be bent from a resting configuration through an arc of 90 degrees, and rebent in the reverse direction an additional 90 degrees to the original resting shape.

Yet another aspect of the present invention is a nonmagnetic surgical needle. The surgical needle has an elongated body, a distal piercing point, and a proximal suture mounting end. The surgical needle is made from ERSTE Type 4456 CA stainless steel alloy which is sufficiently work-hardened such that it has an ultimate tensile strength of at least 250,000 pounds per square inch, and a bending strength in the range of about $7.5 \times 10^{-5}$ inch-pounds to about 8.8 inch-pounds over the range of common needle sizes. The needle has a modulus of elasticity (E) of at least $25 \times 10^6$ pounds per square inch and a yield strength of at least 200,000 pounds per square inch. The needle will have sufficient ductility to effectively permit it to be bent from a resting configuration through an arc of 90 degrees, and rebent in the reverse direction an additional 90 degrees to the original resting shape.

Yet another aspect of the present invention is a method of using the above-described non-magnetic surgical needles in a surgical procedure in the magnetic field of an MRI.

DESCRIPTION OF THE PREFERRED EMBODIMENTS

Figure 1:
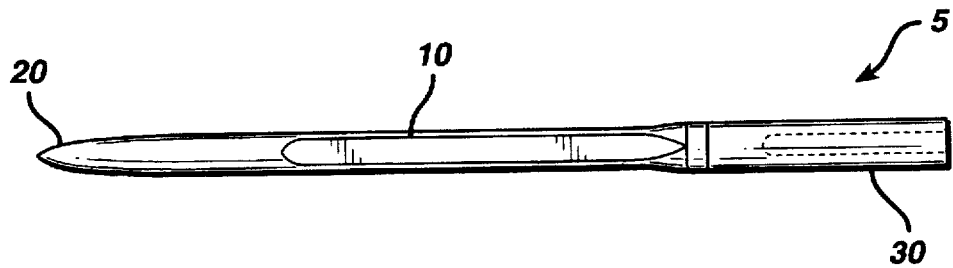
FIG. 1 is a top view of a taper point surgical needle of the present invention.

In most cases, metallic needles are used in the martensitic state. This is true for martensitic, precipitation hardening and 300 grade stainless steel. The martensite in martensitic stainless steel is formed as a result of heat treatment, the martensite in precipitation hardening stainless steel forms athermally and the martensite in 300 grade stainless steels forms as a result of transformation during deformation. The reason is that stainless steel inn the martensitic condition exhibits the best combination of strength and ductility.

The martensite content of the needles makes them magnetic. This is of little or no consequence since the majority of surgical procedures are done in an open environment. If, however, the surgical procedure is done under a magnetic active environment, then the martensite content and resulting magnetism may be a problem.

If the surgical needles are used in a magnetic environment the needles must possess sufficient strength to be practical and still remain non-magnetic. The most likely candidate are the 300 grade stainless steels. These stainless steel alloys contain approximately 18 percent chromium and 8 percent nickel. This grade is non-magnetic in the annealed or soft condition. This is because the microstructure of the alloy is austenite. The strength of the alloy is too low to be practical as a surgical needle. The tensile strength in the annealed condition is about 80,000 pounds per square inch (psi).

In order to strengthen the 300 grade stainless steels it is necessary to subject it to deformation at or near room temperature. This is type of deformation is called cold-working and is usually done by wire drawing. As the amount of cold work increases the strength of the alloy decreases. This is the result of two phenomena. The first is the storage of some part of the energy in microstructure of the alloy. This energy acts as a strengthening mechanism. The second is the conversion of the austenite to martensite. The martensite has a higher strength then the austenite. The stored energy, as seen if deformed grains in the microstructure, does not effect the magnetism of the alloy. The conversion to martensite, however, changes the microstructure from non-magnetic to magnetic. For most austenitic stainless steel, the magnetism or the tensile strength can be used as a measurement of the amount of cold-work in a metallic object.

There is, however, a class of austenitic stainless steels which does not convert to martensite during cold work. This group, exemplified by alloy Type 316 SS, strengthens only by the deformation of the grains during cold-work and no by the transformation to martensite. Because of this, Type 316SS alloy remains non-magnetic even at very high amounts of cold-work. This alloy has the further advantage of being biologically non-reactive with the human body.

Alloy 316SS is a molybdenum-bearing austenitic stainless steel with nickel increased over the level in the plain 18-8 type stainless steel. The elemental composition of Type 316SS alloy is shown in Table 1. Another austenitic alloy composition which shows good strength and is non-magnetic in the cold worked state is ERSTE 4456 CA alloy. This alloy replaces the nickel in the Type 316SS alloy with manganese at a two to one ratio. The chemical composition of 4456 CA is also shown in Table 1.

TABLE 1

| | Chemical Composition (Weight %) | |
|---|---|---|
| | 316SS | 4456CA |
| Chromium | 16.00–18.00 | 16.00–20.00 |
| Nickel | 10.00–14.00 | 0.30 max |
| Molybdenum | 2.00–3.00 | 1.80–2.50 |
| Carbon | 0.08 max | 0.10 max |

TABLE 1-continued

| | Chemical Composition (Weight %) | |
|---|---|---|
| | 316SS | 4456CA |
| Manganese | 2.00 max | 16.00–20.00 |
| Phosphorus | 0.045 max | 0.050 max |
| Sulfur | 0.030 max | 0.050 max |
| Silicon | 1.00 max | 1.00 max |
| Nitrogen | — | 0.70–1.00 |
| Iron | Balance | Balance |

The use of iron based alloy, such as Type 316SS, has the advantage over non-ferrous materials which are also non-magnetic because of its tensile strength and Modulus of Elasticity (E). The tensile strength of cold worked 316SS can be as high as 300,000 psi. Non-ferrous alloys, such as those based on aluminum or titanium, do not usually reach this level. Additionally, the Modulus of Elasticity of 316SS is about $29 \times 10^{+6}$ psi. For aluminum and titanium alloy the Modulus of Elasticity is from 10 to $15 \times 10^{+6}$. This is important since E is a measure of how much the surgical needle will defect under load. During surgery it is disadvantage for a needle to deflect at low loads.

Figure 2:
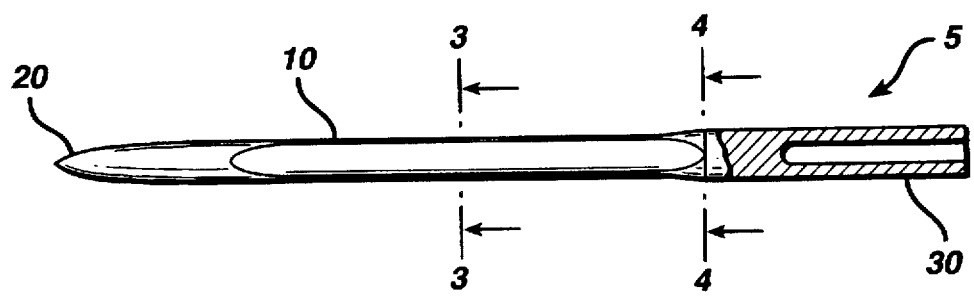
FIG. 2 is a side view of a taper point surgical needle of FIG. 1.
Figure 3:
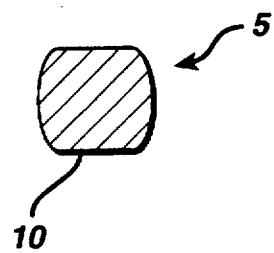
FIG. 3 is a cross-sectional view of the needle of FIG. 2 taken along View Line 3—3.
Figure 4:
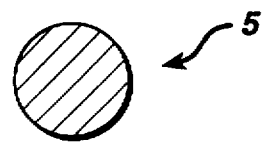
FIG. 4 is a cross-sectional view of the surgical needle of FIG. 2 taken along View Line 4—4.
Figure 5:
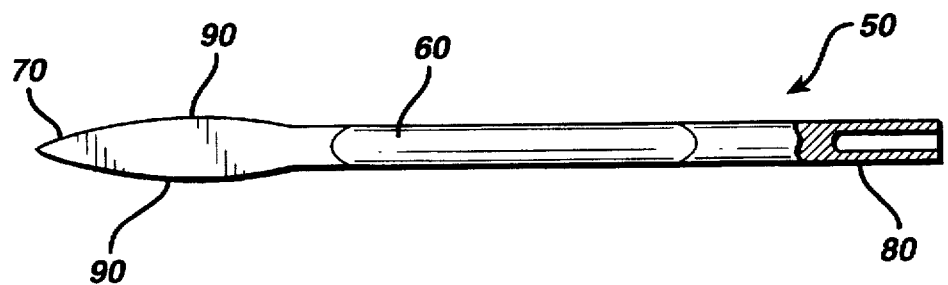
FIG. 5 is a top view of a cutting edge surgical needle of the present invention.
Figure 6:
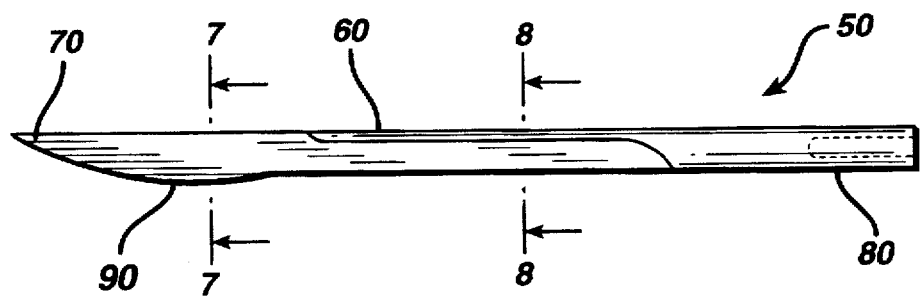
FIG. 6 is a side view of the cutting edge needle of FIG. 5.
Figure 7:
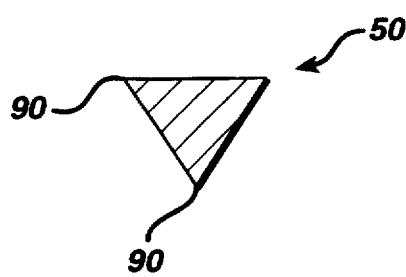
FIG. 7 is a cross-sectional view of the surgical needle of FIG. 6 taken along View Line 7—7.
Figure 8:
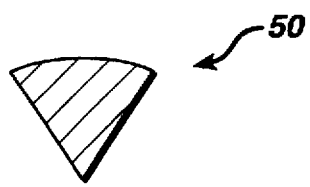
FIG. 8 is a cross-sectional view of the surgical needle of FIG. 6 taken along View Line 8—8.

A taper point surgical needle 5 of the present invention is seen in FIGS. 1–4. The needle 5 is seen to have a conventional configuration having elongated body 10, distal piercing point 20 and proximal suture mounting end 30. A cutting edge needle 50 of the present invention is seen in FIGS. 5–8. Needle 50 has a conventional configuration having elongated body 60, distal piercing point 70, proximal suture mounting end 80 and cutting edges 90.

Methods of manufacturing taper point and cutting edge needles are disclosed in U.S. Pat. No. 5,477,604 and U.S. patent application Ser. No. 08/149,435 filed on Nov. 1, 1993 which are incorporated by reference.

As mentioned above, the needles of the present invention are manufactured from conventional Type 316 stainless steel alloy or ERSTE Type 4456 CA stainless steel alloy. The needles will typically be made from conventional wire sizes having diameters ranging from about 0.00145 inches to about 0.071 inches.

The needles of the present invention are sufficiently work-hardened to effectively impart mechanical characteristics which are substantially equivalent to the mechanical characteristics of magnetic stainless steel alloys such as types 302, 420, and 455 stainless steels, but yet remain nonmagnetic. The terms work-hardened and cold-hardened are interchangeable and are defined to mean the process of increasing a material's strength by forming, stretching or otherwise causing it to undergo plastic, or permanent, deformation, without the addition of heat.

The needles of the present invention are typically work-hardened using the following process. Initially, Type 316SS or ERSTE 4456 CA stainless steel alloy wire rod with a diameter of approximately 0.250 inches is drawn down to progressively smaller diameters into a wire used in the needles manufacturing process. During the reduction process, the metal becomes harder due to a molecular reorientation that takes place, until it becomes too brittle for further drawing. The wire must then be annealed in order to undergo further diameter reductions. By limiting the percent the diameter is reduced between annealing steps to a range of about 90% to about 98%, and the percent reduction after the final anneal to a range of about 93% to about 97%, it is possible to predict the ultimate tensile strength and therefore produce wire that is capable of meeting both the strength and ductility requirements of the needles made from it. Only a very few specific, non-magnetic alloys are capable of undergoing such processing.

The non-magnetic material processed into wire and subsequently needles of the present invention will have the following mechanical characteristics: an ultimate tensile strength of 250,000 pounds per square inch and a yield stress of at least 200,000 pounds per square inch. In addition, the needles will have a modulus of elasticity (E) of at least $25 \times 10^6$ pounds per square inch. The needles will have a bending strength of about $7.5 \times 10^{-5}$ inch-pounds to about 8.8 inch-pounds over the range of typical needle sizing.

The magnetic field strength in a conventional MRI will range from about 1.5 to about 3.0 Telsa. Accordingly, the nonmagnetic needles of the present invention will have to remain nonmagnetic when subjected to these magnetic fields.

The following examples are illustrative of the principles and practice of the present invention, although not limited thereto.

EXAMPLE 1

Stainless steel needles of the present invention having conventional taper point profiles were manufactured in the following manner. The wire raw material was produced in a series of drawing and annealing steps wherein the final drawing diameter reduction after annealing was about 94% to about 96%. The needles were manufactured from the wire in a series of conventional forming and grinding and finishing steps familiar to one skilled in the art.

The needles had the following mechanical characteristics. For a standard needle body cross-section, square in shape, fabricated from Type 316 SS alloy wire with a diameter of 0.025 inches, and cold-worked during the drawing process as described above, the bending strength of the needle was 0.66 inch-pounds, and the ductility was sufficient to permit the needle to be bent from a resting position through an arc of 90 degrees and rebent in the reverse direction another 90 degrees to its original shape (a conventional ductility test in the surgical needle arts). In addition, the needle was not significantly influenced by a 1.5 Telsa magnet of the type standard to MRI. For a needle with a round body cross-section fabricated with Type 316 SS alloy wire having a diameter of 0.022 inches, and cold-worked as described above, the bending strength was 0.64 inch-pounds and ductility is as described above. This needle was also not significantly influenced by a 1.5 Telsa magnet.

EXAMPLE 2

A surgical needle of the present invention is utilized by a surgeon to perform a craniotomy procedure on a patient in a conventional interventional MRI unit in the following manner. The surgeon makes an incision in the skin an subcutaneous tissue of the scalp to expose the cranium. A portion of the cranium is then removed and an additional incision is made in the dura layer exposing the brain. When the biopsy or other surgical procedure in the brain is completed, surgical needles of the present invention having conventional surgical sutures mounted thereto, are used by the surgeon to close the incision in the dura and skin in a conventional manner by inserting the needles through the tissue surrounding the incisions a sufficient number of times to effectively approximate the tissue with the sutures. The use of the non-magnetic needles of the present invention prevents the needles from moving or otherwise being displaced by the magnetic field of the MRI unit both when they are and are not being grasped by the surgeon, as is routinely necessary in normal suturing practice.

It is surprising and unexpected that surgical needles can be made from stainless steel alloys which are substantially non-magnetic when placed in the magnetic field of a conventional MRI diagnostic unit. It is surprising and unexpected that surgical needles made from Type 316 and ERSTE 4456 CA stainless steel alloys can be work-hardened to have similar mechanical characteristics to conventional stainless steel alloy needles.

Although this invention has been shown and described with respect to detailed embodiments thereof, it will understood by those skilled in the art that various changes in form and detail thereof may be made without departing from the spirit and scope of the claimed invention.

We claim:

1. A non-magnetic surgical needle comprising an elongated member having a distal piercing tip and a proximal suture mounting end, said needle comprising Type 316 stainless steel, wherein said needle is work-hardened and has the following mechanical characteristics:

a modulus of elasticity (E) of at least $25 \times 10^6$ pounds per square inch;

an ultimate tensile strength of at least 250,000 pounds per square inch;

a yield strength of at least 200,000 pounds per square inch;

a bending strength of about $7.5 \times 10^{-5}$ inch-pounds to about 8.8 inch-pounds; and, sufficient ductility to such that the needle can be effectively be bent from a resting shape through an arc of 90 degrees, and rebent in the reverse direction an additional 90 degrees back to the resting shape, wherein said needle is non-magnetic in the magnetic field of a 1.5 Telsa magnet.

2. A non-magnetic surgical needle comprising an elongated member having a distal piercing tip and a proximal suture mounting end, said needle comprising ERSTE Type 4456 CA stainless steel alloy, wherein said needle is work hardened and has the following mechanical characteristics:

a modulus of elasticity (E) of at least $25 \times 10^6$ pounds per square inch;

an ultimate tensile strength of at least 250,000 pounds per square inch;

a yield strength of at least 200,000 pounds per square inch;

a bending strength of about $7.5 \times 10^{-5}$ inch pounds to about 8.8 inch-pounds; and, sufficient ductility to such that the needle can be effectively be bent from a resting shape through an arc of 90 degrees, and rebent in the reverse direction an additional 90 degrees back to the resting shape, wherein said needle is non-magnetic in the magnetic field of a 1.5 Telsa magnet.

3. A method of suturing tissue in the magnetic field of an MRI diagnostic unit, said method comprising:

passing a surgical needle and attached suture through tissue a sufficient number of times to effectively approximate the tissue, said surgical needle comprising:

a non-magnetic surgical needle having an elongated member having a distal piercing tip and a proximal suture mounting end, said needle comprising Type 316 stainless steel, wherein said needle is work hardened and has the following mechanical characteristics:
- a modulus of elasticity (E) of at least $25\times10^6$ pounds per square inch;
- an ultimate tensile strength of at least 250,000 pounds per square inch;
- a yield strength of at least 200,000 pounds per square inch;
- a bending strength of about $7.5\times10^{-5}$ inch-pounds to about 8.8 inch-pounds; and,
- sufficient ductility to such that the needle can be effectively be bent from a resting shape through an arc of 90 degrees, and rebent in the reverse direction an additional 90 degrees back to the resting shape,
- wherein said needle is non-magnetic in the magnetic field of a 1.5 Telsa magnet.

4. A method of suturing tissue in the magnetic field of an MRI diagnostic unit, said method comprising:
passing a surgical needle and attached suture through tissue a sufficient number of times to effectively approximate the tissue, said surgical needle comprising:
a non-magnetic surgical needle having an elongated member having a distal piercing tip and a proximal suture mounting end, said needle comprising ERSTE 4456 CA stainless steel alloy, wherein said needle is work hardened and has the following mechanical characteristics:
- a modulus of elasticity (E) of at least $25\times10^6$ pounds per square inch;
- an ultimate tensile strength of at least 250,000 pounds per square inch;
- a yield strength of at least 200,000 pounds per square inch;
- a bending strength of about $7.5\times10^{-5}$ inch-pounds to about 8.8 inch-pounds; and,
- sufficient ductility to such that the needle can be effectively be bent from a resting shape through an arc of 90 degrees, and rebent in the reverse direction an additional 90 degrees back to the resting shape,
- wherein said needle is non-magnetic in the magnetic field of a 1.5 Telsa magnet.

* * * * *